United States Patent [19]
Harris

[11] Patent Number: 5,531,226
[45] Date of Patent: Jul. 2, 1996

[54] UROGENITAL MUSCLE EXERCISE SENSOR SYSTEM

[76] Inventor: Howard T. Harris, 2235 Whiteback, Houston, Tex. 77084

[21] Appl. No.: 329,665

[22] Filed: Oct. 26, 1994

Related U.S. Application Data

[63] Continuation-in-part of Ser. No. 917,786, Jul. 20, 1992, abandoned, which is a continuation-in-part of Ser. No. 683,558, Apr. 10, 1991, abandoned.

[51] Int. Cl.⁶ .................................................. A61B 5/103
[52] U.S. Cl. .................................................. 128/774
[58] Field of Search .................................. 128/644, 733, 128/734, 774, 778, 782

[56] References Cited

U.S. PATENT DOCUMENTS

| | | | |
|---|---|---|---|
| 4,256,118 | 3/1981 | Nagel | 128/733 |
| 4,258,720 | 3/1981 | Flowers | 128/774 |
| 4,709,704 | 12/1987 | Lukasiewicz | 128/644 |
| 4,729,377 | 3/1988 | Granek et al. | 128/644 |
| 4,909,263 | 3/1990 | Norris | 128/778 |
| 4,913,162 | 4/1990 | Leang et al. | 128/774 |
| 4,949,729 | 8/1990 | Haski | 128/774 |
| 4,989,615 | 2/1991 | Hochberg | 128/778 |

*Primary Examiner*—Max Hindenburg

[57] ABSTRACT

Urogenital muscle exercise sensor system located totally external to the human body to provide muscular feedback. The sensor system comprises a self-resilient hollow bag which resiliently expands to its initial shape after compression, a feedback means for providing feedback to the user, a connection meand for connecting the self-resilient hollow gab to the feedback means, a fluid means within the self-resilient hollow bag and connection means for transmitting pressure from the hollow bag to the feedback means, and attachment means with pocket means for the insertion of the hollow bag therein for attaching the exercise sensor system to the human body.

26 Claims, 2 Drawing Sheets

UROGENITAL MUSCLE EXERCISE SENSOR SYSTEM

This application is a Continuation-In-Part of Ser. No. 07/917,786 filed Jul. 20, 1992, now abandoned, which is a Continuation-In-Part Application of the Parent Application Ser. No. 07/683,558, filed on 10 Apr. 1991, titled "Urogenital Muscle Exercise Sensor System", now abandoned.

BACKGROUND

1. Field of Invention

This invention relates to the urogenital muscles, specifically to a more safe and improved method of feedback concerning the exercising of these muscles. A fully functioning prototype is already in existance.

2. Discussion of Prior Art

Heretofore, the urogenital muscle exercisers have had some sort of probe that has to be inserted into the person's body. The probe is used to measure the pressure exerted on it by the muscles. When the female uses the device, the probe has to be inserted into her vagina. Some of these devices can be used by a male inserting the probe up his rectum. Examples of prior art are U.S. Pat. No. 2,507,858 and U.S. Pat. No. 2,541,520 both to Kegel, U.S. Pat. No. 3,640,284 to De Langis, U.S. Pat. No. 3,752,150 to Harris, U.S. Pat. No. 4,050,449 to the assignee of Medical Products Development Corporation.

Disadvantages of the prior art, which are caused by the probe that must be inserted into the body are;

one has phallic fear or masturbatory guilt, the prior art is harder to use, the probe has to be meticulously cleaned between uses.

An advantage over Hochberg's U.S. Pat. No. 4,989,615 is that this invention provides a bladder-like means that has NO need for a resilient-insert element. As a result, there is nothing inside the bladder-like means that could move around or otherwise cause trouble with the functioning of the device. Thus, there is an OMISSION OF AN ELEMENT.

Self-resiliency of the said bladder-like means can be gained by making the walls of the bladder-like means out of, or coated with, a rubber-like material or plastic-like material that has resilient characteristics. This will give the bladder-like means the UNEXPECTED RESULT of being SELF-RESILIENT.

SUMMARY—OBJECTS AND ADVANTAGES

Some advantages of this invention over the prior art are:

There is no probe to meticulously clean between each use,

In the embodiment shown, the pants can be separated from the rest of the device, and cleaned, very easily. This can be done by separating (the part of the bladder-like means assembly that is on the outside of the pants) from (the part of the bladder-like means assembly that is on the inside of the pants) and washing the pants in a washer and dryer. The said separation can be done in three steps. To see how this can be done, look at FIG. 4.

The first step is to separate the bladder-like means, item number 18, from the tee, item number 19.

The second step is to separate (the group consisting of item numbers 19, 20, 21, and 22) from the pants. This can be done by separating the two halves of the velcro, item number 11 of FIG. 1. (Item number 11 shows both genders of the velcro stuck together).

The third step is to take the bladder-like means, item number 26 of FIG. 1, out of the pocket, item number 10A of FIG. 1.

What is left is shown as FIG. 2. FIG. 2 is put in the washer and dryer as one would an ordinary pair of pants.

One does not have any phallic fear or mastubatory guilt using this invention because there is not anything inserted into one's body.

Having strong urogenital muscles helps:

the individual to have greater sexual satisfaction, the individual to have better bladder control, the female to have an easier and safer time of delivery while giving birth to her child. This is because she will have more control when to and when not to push the baby out of her vagina during delivery.

One object of this invention is to provide a device that can be used by either a male or female to strengthen urogenital muscles with feedback being provided that indicates the status of the exercises being performed.

Still another object of this invention is to provide an EASIER device for urogenital muscle exercises to be done with.

Still another object of this invention is to provide a SAFER device for urogenital muscle exercises to be done with. This invention is safer than the other urogenital muscle exercise inventions because there are no injuries that can happen as a result of using a probe that has to be placed inside the body.

Still another object of this invention is to provide a way to do these urogenital exercises with MORE COMFORT while using the device because there is no part of the device that is placed into the body.

Still another object of this invention is to provide an apparatus of this type that is well suited otherwise to its intended function.

BRIEF DESCRIPTION OF THE DRAWINGS OF THE EMBODIMENT SHOWN

FIG. 9 shows how each wall of the bladder-like means is in position with relation to the torso the bladder-like means is held to.

DESCRIPTION OF THE PREFERRED EMBODIMENT

This invention works on the basis that urogenital muscle activity inside the body causes pressure changes that can be felt not only inside the body, but also as minute changes in the form of movement, or skin bulges, on the outside of the body. These said minute skin movements or bulges on the outside of the body causes pressure changes in a device, such as a bladder-like means, that is placed against the urogenital part of the outside of the body. The bladder-like means may be filled with either a gas, jelly, or liquid, or any combination of these. The change in pressure in this said bladder-like means is felt by a sensor, and a feedback value of some sort is given to the individual exercising.

The main sections of this embodiment are the pants, bladder-like means assembly, and feedback section. For explanation purposes, I have included the said feedback section as a part of the bladder-like means assembly.

Figure 9:
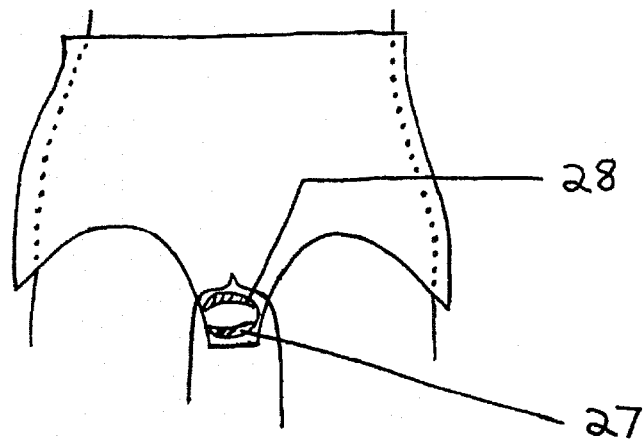

The pants is only one way that exists in which the bladder-like means can be placed and held against the body. However, the method that is chosen must also keep a pressure against the wall of the bladder-like means, item number 27 of FIG. 9, that is opposite the wall of the bladder-like means, item number 28 of FIG. 9, that is against the urogenital area.

Figure 1:
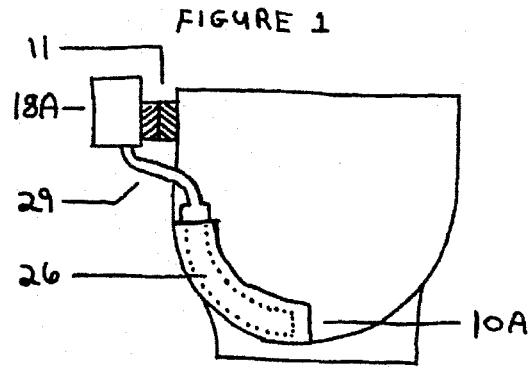
FIG. 1 is the top assembly—view from the SIDE of the pants.
Figure 3:
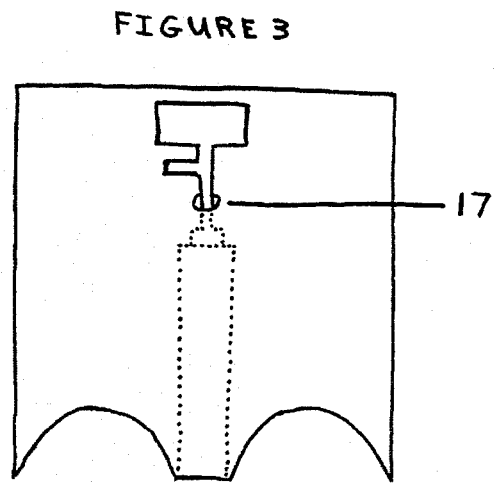
FIG. 3 is the view of the top assembly from the OUTSIDE of the front of the pants.

FIG. 1 and FIG. 3, each show the top assembly from different views.

Figure 2:
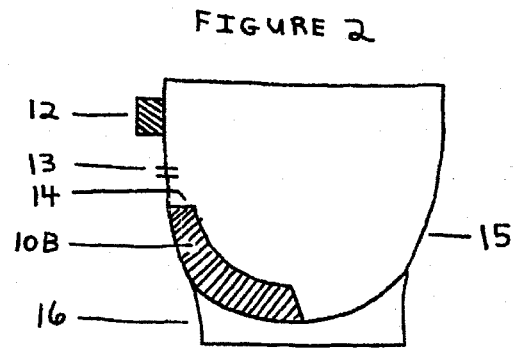
FIG. 2 is the view of the PANTS ALONE from the side.
Figure 4:
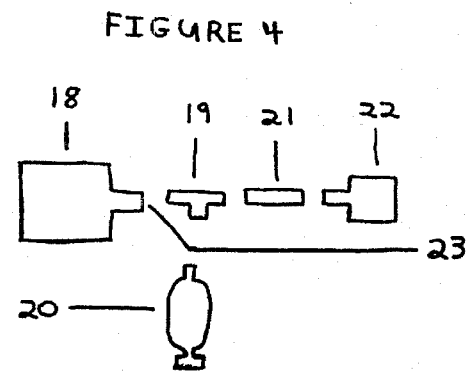
FIG. 4 is the bladder-like means assembly.

The top assembly consists of the following:
   the pants, which is shown as FIG. 2, and
   the bladder-like means assembly and feedback section, which is shown as FIG. 4.

The pants are designed as the following:
   one gender of velcro is sewn onto the pants in the location as shown by item number 12 of FIG. 2.

A hole is placed in the pants in the location as shown by item number 13 of FIG. 2 and by the other view by item number 17 of FIG. 3.

The pocket is placed on the inside of the pants IN THE UROGENITAL AREA with the opening at the top. The pocket is shown as item number 10B of FIG. 2. The opening of the pocket is shown as item number 14 of FIG. 2.

The torso of the pants is shown as item number 15 of FIG. 2.

The legs of the pants is shown as item number 16 of FIG. 2.

The bladder-like means assembly of FIG. 4 consists of the following:

The bladder-like means as shown by item number 18.

A tee as shown by item number 19.

A valve that will let the said bladder-like means be filled with liquid, or gas, or jelly and will hold the desired substance into the said bladder-like means assembly, as long as is desired by the individual using the invention. This said valve is item number 20 of FIG. 4.

The tubing, item number 21 of FIG. 4.

The feedback section as shown by item number 22 of FIG. 4.

The insert-element of Hochberg's U.S. Pat. No. 4,989,615 is OMITTED.

A valve, item number 20 of FIG. 4, needs to be added to the said bladder-like means assembly to assist the individual in changing the amount of fluid pressure that is inside the said bladder-like means assembly.

The fluid pressure in the said bladder-like means assembly can be changed by opening the valve, item number 20 of FIG. 4, then changing the amount of fluid inside the said bladder-like means assembly. When the proper amount of pressure is in the said bladder-like means assembly, the valve, item number 20 of FIG. 4 needs to be closed.

The said bladder-like means assembly is placed onto the pants as follows:

The bladder-like means, item number 18 of FIG. 4, is separated from the tee, item number 19 of FIG. 4.

It was mentioned above that one gender of the velcro is sewn onto the pants. The other gender of the matching velcro is glued onto the feedback section. The feedback section is placed onto the pants by putting the two genders of the velcro together as shown by item number 11 of FIG. 1.

The bladder-like means, item number 26 of FIG. 1, is placed into the pocket, item number 10A of FIG. 1.

The opening of the bladder-like means, item number 23 of FIG. 4, is placed through the hole in the pants, item number 13 of FIG. 2 and onto the tee, item number 19 of FIG. 4.

The device of the embodiment shown is put on in the same manner that a pair of pants is put on.

FIG. 1 shows the completed device. Notice that FIG. 5, FIG. 6, and FIG. 7 show the human body in the suit as shown from the same view as seen in FIG. 1.

Figure 5:
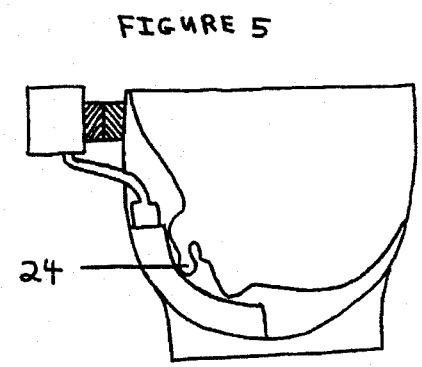
FIG. 5 is the position of the MALE wearing the device for Exercise A.

FIG. 5 shows how the male wears the suit for Exercise A. Notice the penis is in the down position, as shown by item number 24. This exercise is performed by the male trying to press his penis, which is already against the bladder-like means, further into or towards the bladder-like means. This results in a pressure change within the bladder-like means. The bladder-like means will then relay this pressure change to the feedback section. The feedback section then provides the feedback to the individual.

Figure 6:
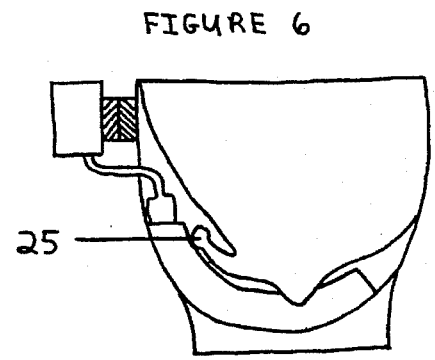
FIG. 6 is the position of the MALE wearing the device for Exercise B and Exercise C.
Figure 7:
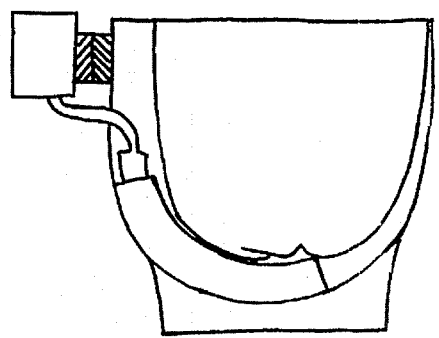
FIG. 7 is the view of the FEMALE wearing the device as seen from the side.

FIG. 6 shows how the male wears the suit for Exercise B and Exercise C. Notice the penis is in the up position for both exercises, as shown by item 25.

The urogenital muscles that are between the testicles and the anus can be flexed. This said flexing of these said muscles causes a change of pressure in the said bladder-like means. The said bladder-like means will then relay this said pressure change to the feedback section. The feedback section then provides the feedback to the individual using the device. This is Exercise B.

Exercise C is done by flexing the muscles of the penis, as though one were cutting off the flow of urine. As the penis is against the said bladder-like means, this flexing of these muscles will cause the pressure in the said bladder-like means to change. The said bladder-like means will then relay this pressure change to the feedback section. The feedback section then provides the feedback to the individual using the device.

Figure 8:
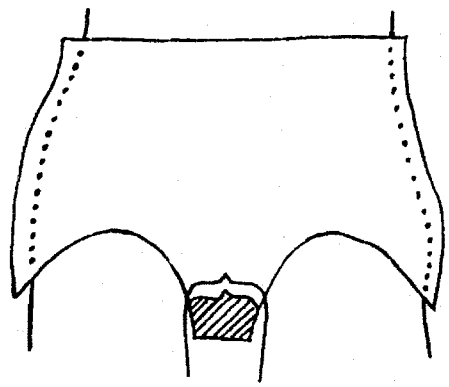
FIG. 8 is the position of the FEMALE wearing the device as seen from the front.

FIG. 7 and FIG. 8, both show how the female wears the device for Exercise D and Exercise E.

FIG. 7 shows the position of the female while wearing the suit as shown by the same view as seen by FIG. 1. FIG. 8 shows the female wearing the suit as seen from the front view. The exercise is done by the female flexing her muscles that she uses to stop urine from flowing when she is urinating. The flexing of these said muscles causes the outer skin covering her urogenital area to move. This movement of the outer skin causes a change in the pressure inside the bladder-like means, which is placed against the female's urogenital area. The bladder-like means will then relay this pressure change to the feedback section. The feedback section then provides the feedback to the individual using the device. This is Exercise D.

Exercise E can be done by the female flexing the muscles of her vagina. This flexing of these said muscles causes the outer skin covering her urogenital area to move. This movement of the outer skin causes a change in the pressure inside the bladder-like means, which is placed against the female's urogenital area. The bladder-like means will then relay this said pressure change to the feedback section. The feedback section then provides the feedback to the individual using the device.

Thus, the reader will see that this invention is more safe to use than other urogenital muscle exercise sensor systems. There is NOT any part of this invention that is inserted into the body in any manner.

The said bladder-like means has no insert-element that could move around or otherwise cause trouble with the functioning of the device. So the reader can see that the said bladder-like means of this invention is an improvement of the said bladder-like means of Hochberg's U.S. Pat. No. 4,989,615. The said bladder-like means of this invention has an OMISSION OF AN ELEMENT.

In addition, with at least one wall of the said bladder-like means being made of, or coated with, a rubber-like material or plastic-like material of resilient characteristics, self-resiliency can be gained.

While my above description contains many specificities, these should NOT be construed as limitations on the scope of the invention, but rather as exemplifications of PREFERRED embodiments thereof. Many other variations are possible.

Accordingly, the scope of the invention should be determined NOT by the examples illustrated, but by the claims and their equivalents.

I claim:

1. A urogenital muscle exercise sensor system externally located on a human body to provide muscular feedback to the user comprising:

a self-resilient hollow bag means which resiliently expands to its initial shape after compression, a feedback means for providing a feedback to the user, a connection means for connecting said self-resilient hollow bag means to said feedback means, a fluid means within said self-resilient hollow bag means and connection means for transmitting pressure from said self-resilient hollow bag means to said feedback means, and attachment means with pocket means for the insertion of said self-resilient hollow bag means therein for attaching said urogenital muscle execise sensor system to the body, whereby said pocket means with said self-resilient hollow bag means is located against the external genital part of the body and muscles exercised in this body area will place pressure on said self-resilient hollow bag means which will be shown to the user by said feedback means.

2. A urogenital muscle exercise sensor system as claimed in claim 1 wherein said connection means includes a tube and a tee.

3. A urogenital muscle exercise sensor system as claimed in claim 2 wherein said tee includes an opening means for said fluid means.

4. A urogenital muscle exercise sensor system as claimed in claim 1 wherein said attachment means includes pants.

5. A urogenital muscle exercise sensor system as claimed in claim 2 wherein said self-resilient hollow bag means, said tube, said tee, and said feedback means are detachable from one another.

6. A urogenital muscle exercise sensor system as claimed in claim 1 wherein said attachment means and said feedback means having interacting engagement means.

7. A urogenital muscle exercise sensor system externally located on a human body to provide muscular feedback to the user comprising:

a bladder-like means containing pressure, a feedback means for providing a feedback to the user, a connection means for connecting said bladder-like means to said feedback means, a fluid means within said bladder-like means and connection means for transmitting pressure from said bladder-like means to said feedback means, and holding means for holding said bladder-like means in position to be adapted to contact the urogenital area of said human body; and muscles exercised in this body area places pressure, or a change in pressure, on said bladder-like means; and said pressure, or change in pressure, on said bladder-like means enables said urogenital muscle exercise sensor system to provide said feedback to the user.

8. A urogenital muscle exercise sensor system as claimed in claim 7 wherein said connection means includes a tube and a tee.

9. A urogenital muscle exercise sensor system as claimed in claim 8 wherein said tee includes an opening means for said fluid means.

10. A urogenital muscle exercise sensor system as claimed in claim 7 wherein said holding means includes pants.

11. A urogenital muscle exercise sensor system as claimed in claim 7 wherein said holding means and said feedback means having interacting engagement means.

12. A urogenital muscle exercise sensor system as claimed in claim 7 wherein said holding means includes strapping.

13. A urogenital muscle exercise sensor system as claimed in claim 7 wherein said holding means includes a hook-like means.

14. A urogenital muscle exercise sensor system as claimed in claim 7 wherein said bladder-like means is made of, or coated with, a rubber-like material, or a plastic-like material, that is of resilient characteristics, making said bladder-like means self-resilient.

15. A urogenital muscle exercise sensor system as claimed in claim 7 wherein said means to keep bladder-like means in proper position includes means to seat said holding means.

16. A urogenital muscle exercise sensor system as claimed in claim 7 wherein said holding means includes a framing means for holding said bladder-like means.

17. A urogenital muscle exercise sensor system totally external to the human body to provide muscular feedback to the user comprising:

a bladder-like means containing pressure, a feedback means for providing feedback to the user, a connection means for connecting said bladder-like means to said feedback means, a fluid means within said bladder-like means and connection means for transmitting pressure from said bladder-like means to said feedback means, and holding means for holding said bladder-like means in position to be adapted to contact a material such as, but not limited to, garment or cloth, which is adapted to contact the urogenital area of said human body; and muscles exercised in this body area places pressure, or a change in pressure, on said bladder-like means; and said pressure, or change in pressure, on said bladder-like means enables said urogenital muscle exercise sensor system to provide said feedback to the user.

18. A urogenital muscle exercise sensor system as claimed in claim 17 wherein said holding means includes a hook-like means.

19. A urogenital muscle exercise sensor system as claimed in claim 17 wherein said connection means includes a tube and a tee.

20. A urogenital muscle exercise sensor system as claimed in claim 17 wherein said holding means and said feedback means have interacting engagement means.

21. A urogenital muscle exercise sensor system as claimed in claim 17 wherein said bladder-like means is made of, or coated with, a rubber-like material, or a plastic-like material, that is of resilient characteristics, making said bladder-like means self-resilient.

22. A urogenital muscle exercise sensor system as claimed in claim 17 wherein said means to keep bladder-like means in proper position includes means to seat said holding means.

23. A urogenital muscle exercise sensor system as claimed in claim 17 wherein said holding means includes a framing means for holding said bladder-like means.

24. A urogenital muscle exercise sensor system as claimed in claim 19 wherein said tee includes an opening means for said fluid means.

25. A urogenital muscle exercise sensor system as claimed in claim 17 wherein said holding means includes pants.

26. A urogenital muscle exercise sensor system as claimed in claim 17 wherein said holding means includes strapping.

* * * * *